(12) United States Patent
Pakenham et al.

(10) Patent No.: US 10,259,987 B2
(45) Date of Patent: Apr. 16, 2019

(54) AMINE ADDUCTS, DERIVATIVES THEREOF, METHODS FOR MAKING SUCH ADDUCTS AND DERIVATIVES, AND METHODS FOR USING SUCH ADDUCTS AND DERIVATIVES

(71) Applicants: Derek Pakenham, Hamilton, NJ (US); Mikal Morvan, Pessac (FR); Guillaume Degre, Talence (FR)

(72) Inventors: Derek Pakenham, Hamilton, NJ (US); Mikal Morvan, Pessac (FR); Guillaume Degre, Talence (FR)

(73) Assignee: RHODIA OPERATIONS, Aubervilliers (FR)

( * ) Notice: Subject to any disclaimer, the term of this patent is extended or adjusted under 35 U.S.C. 154(b) by 240 days.

(21) Appl. No.: 13/724,537

(22) Filed: Dec. 21, 2012

(65) Prior Publication Data

US 2013/0161014 A1 Jun. 27, 2013

Related U.S. Application Data

(60) Provisional application No. 61/578,390, filed on Dec. 21, 2011.

(51) Int. Cl.
*C09K 8/584* (2006.01)
*C11D 1/62* (2006.01)
(Continued)

(52) U.S. Cl.
CPC ............ *C09K 8/584* (2013.01); *C07C 227/02* (2013.01); *C07C 231/14* (2013.01);
(Continued)

(58) Field of Classification Search
CPC ......... C09K 8/584; C09K 8/602; E21B 43/16; E21B 43/26; C11D 1/62; C11D 1/90; C11D 1/92; C07C 227/02; C07C 233/38; C07C 233/39; C07C 303/20; C07C 309/14
(Continued)

(56) References Cited

U.S. PATENT DOCUMENTS 3,199,586 A 8/1965 Henderson et al.
3,260,669 A 7/1966 Schoen
(Continued)

FOREIGN PATENT DOCUMENTS

WO 2009130170 A1 10/2009
WO 2010105879 A1 9/2010

*Primary Examiner* — Aiqun Li

(57) ABSTRACT

An amine adduct is made by (1) forming an addition intermediate by heating a mixture comprising at least one diene and at least one unsaturated fatty acyl compound, and reacting the addition intermediate with a diamine to form the amine adduct, or by (2) reacting at least one unsaturated fatty acyl compound with at least one diamine to form an amine intermediate, and heating a mixture of the amidoamine intermediate and at least one diene to form the amine adduct, or by (3) reacting at least one unsaturated fatty tertiary amine compound with at least at least one diene to form the amine adduct. A surfactant composition is derived from the amine adduct and is particularly useful in a method for enhancing the recovery of oil from a reservoir having a production wellbore, comprising introducing an aqueous flooding fluid into the reservoir at one or more locations different from the location of the production wellbore, said fluid comprising the surfactant composition and recovering the oil through the production wellbore.

5 Claims, 6 Drawing Sheets

(51) Int. Cl.

| | | |
|---|---|---|
| *C11D 1/90* | (2006.01) | |
| *C11D 1/92* | (2006.01) | |
| *E21B 43/26* | (2006.01) | |
| *E21B 43/16* | (2006.01) | |
| *C07C 227/02* | (2006.01) | |
| *C07C 231/14* | (2006.01) | |
| *C07C 309/14* | (2006.01) | |
| *C07C 303/20* | (2006.01) | |
| *C07C 233/38* | (2006.01) | |
| *C11D 1/94* | (2006.01) | |
| *C07C 233/39* | (2006.01) | |

(52) U.S. Cl.
CPC .......... *C07C 233/38* (2013.01); *C07C 233/39* (2013.01); *C07C 303/20* (2013.01); *C07C 309/14* (2013.01); *C11D 1/94* (2013.01); *E21B 43/16* (2013.01); *E21B 43/26* (2013.01); *C11D 1/62* (2013.01); *C11D 1/90* (2013.01); *C11D 1/92* (2013.01); *Y10T 137/0318* (2015.04)

(58) Field of Classification Search
USPC .................................. 507/255, 259
See application file for complete search history.

(56) References Cited

U.S. PATENT DOCUMENTS

| | | | | |
|---|---|---|---|---|
| 3,850,611 | A | * | 11/1974 | Nakanishi .................... 504/224 |
| 5,368,758 | A | * | 11/1994 | Gapinski ............. C10M 135/00 |
| | | | | 508/273 |
| 6,258,859 | B1 | | 7/2001 | Dahanayake et al. |
| 6,979,744 | B1 | | 12/2005 | O'Lenick, Jr. et al. |
| 7,461,694 | B2 | | 12/2008 | Dahanayake et al. |
| 2005/0227876 | A1 | | 10/2005 | Hellsten et al. |
| 2006/0217286 | A1 | * | 9/2006 | Geoffroy .............. C11D 3/3796 |
| | | | | 510/490 |
| 2007/0142235 | A1 | | 6/2007 | Berger et al. |
| 2008/0194738 | A1 | * | 8/2008 | Crews ..................... C04B 26/26 |
| | | | | 524/60 |
| 2010/0096139 | A1 | * | 4/2010 | Holcomb et al. .......... 166/308.1 |

* cited by examiner

AMINE ADDUCTS, DERIVATIVES THEREOF, METHODS FOR MAKING SUCH ADDUCTS AND DERIVATIVES, AND METHODS FOR USING SUCH ADDUCTS AND DERIVATIVES

FIELD OF THE INVENTION

This invention relates to amine adducts, derivatives thereof, methods for making such adducts and derivatives, and methods for using such adducts and derivatives, more particularly, a method for enhancing recovery of oil from a reservoir.

BACKGROUND OF THE INVENTION

Amidoamines derived from DMAPA and a vegetable oil, such as soybean oil, are known as intermediates used in the manufacture of derivatives such as betaines, sulfobetaines & amine oxides. The performance of these types of materials employed as surfactants in a wide variety of applications in many fields of interest, such as industrial processes, personal care, home care, oil production, is known, but there is a continuing interest in improved surfactant compounds that provide enhanced properties of improved efficiency for more economical use.

One application for such surfactants is in oil recovery processes, such as fracturing processes, as disclosed in, for example, U.S. Pat. No. 6,258,859, issued Jul. 10, 2001 to Manilal Dahayanake, et. al., and flooding processes, as disclosed, for example, in U.S. Pat. No. 3,199,586, issued Aug. 10, 1965 to James Henderson, et. al., and U.S. Pat. No. 7,461,694, issued Dec. 9, 2008, to Manilal Dahayanake, et. al.

SUMMARY OF THE INVENTION

In a first aspect, the present invention is directed to an amine adduct, comprising the product obtained by:
(1)(a) forming an addition intermediate by heating a mixture comprising at least one diene and at least one unsaturated fatty acyl compound, and
  (b) reacting the addition intermediate with a diamine to form the amine adduct, or
(2)(a) reacting at least one unsaturated fatty acyl compound with at least one diamine to form an amidoamine intermediate, and
  (b) heating a mixture of the amidoamine intermediate and at least one diene to form the amine adduct, or
(3) reacting at least one unsaturated fatty tertiary amine compound with at least at least one diene to form the amine adduct.

In one embodiment, the amine adduct is the amidoamine product obtained by:
(1)(a) forming an addition intermediate by heating a mixture comprising at least one diene and at least one unsaturated fatty acyl compound, and
  (b) reacting the addition intermediate with a diamine to form the amidoamine product, or
(2)(a) reacting at least one unsaturated fatty acyl compound with at least one diamine to form an amidoamine intermediate, and
  (b) heating a mixture of the amidoamine intermediate and at least one diene to form the amidoamine product.

In another embodiment, the amine adduct is the amine product obtained by reacting at least one unsaturated fatty tertiary amine compound with at least at least one diene to form the amine product.

In a second aspect, the present invention is directed to a process for making an amine adduct, comprising:
(1)(a) forming an addition intermediate by heating a mixture of at least one diene and at least one unsaturated fatty acyl compound, and
  (b) reacting the addition intermediate with at least one diamine to form the amine adduct, or
(2)(a) reacting at least one unsaturated fatty acyl compound with at least one diamine to form an amine intermediate, and
  (b) heating a mixture of the amidoamine intermediate and at least one diene to form the amine adduct, or
(3) reacting at least one unsaturated fatty tertiary amine compound with at least at least one diene to form the amine adduct.

In one embodiment, the amine adduct is an amidoamine product and the process comprises:
(1)(a) forming an addition intermediate by heating a mixture of at least one diene and at least one unsaturated fatty acyl compound, and
  (b) reacting the addition intermediate with at least one diamine to form the amidoamine product, or
(2)(a) reacting at least one unsaturated fatty acyl compound with at least one diamine to form an amidoamine intermediate, and
  (b) heating a mixture of the amidoamine intermediate and at least one diene to form the amidoamine product.

In another embodiment, the amine adduct is an amine product and the process comprises reacting at least one unsaturated fatty tertiary amine compound with at least at least one diene to form the amine product.

In a third aspect, the present invention is directed to a surfactant composition comprising at least one surfactant compound derived from an amine adduct of the present invention.

In one embodiment, the surfactant composition comprises at least one surfactant compound derived from the amidoamine product of the present invention.

In another embodiment, the surfactant composition comprises at least one surfactant compound derived from the amine product of the present invention.

In an fourth aspect, the present invention is directed to a surfactant composition, comprising at least one surfactant compound according to structure (I):

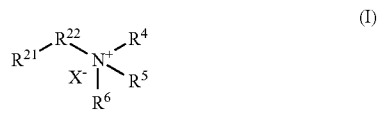

wherein:
$R^{21}$ is an is an adduct of at least one diene, typically a $(C_4-C_{20})$diene, and at least one unsaturated fatty hydrocarbon group,
$R^{22}$ is —$CH_2$— or an acylamido radical according to the structure:

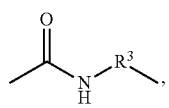

$R^3$ is a divalent hydrocarbon radical, optionally substituted on one or more carbon atoms with hydroxyl, more typically a straight chain or branched chain ($C_2$-$C_6$)alkylene radical, optionally substituted on one or more carbon atoms with hydroxyl, $R^4$ and $R^5$ are each independently alkyl, cycloalkyl, aryl, or aralkyl, or may be fused to form, together with the nitrogen atom to which they are each attached, form a heterocyclic 4 to 8 membered ring, or, if $R^{22}$ is —$CH_2$—, may be hydrogen-terminated alkyleneoxy, $R^6$ is absent or is H, alkyl, cycloalkyl, alkenyl, aralkyl, $O^-$, —$(CH_2)_n$—$COO^-$, or

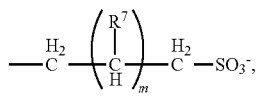

each $R^7$ is independently H or hydroxyl, n is an integer of from 1 to 4, m is an integer of from 0 to 4, more typically, of from 1 to 4, and $X^-$ is an anionic counterion, and further provided that:

if $R^6$ is absent, then the positive charge is absent from the nitrogen atom to which $R^4$ and $R^5$ are each attached and the $X^-$ counterion is absent, and if $R^6$ is $O^-$, —$(CH_2)_n$—$COO^-$, or

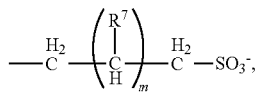

then $X^-$ counterion is absent.

In one embodiment, the surfactant composition comprises at least one surfactant compound according to structure (II):

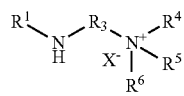 (II)

wherein:

$R^1$ is an acyl radical according to the structure:

$R^2$ is an adduct of at least one diene, typically a ($C_4$-$C_{20}$) diene, and at least one unsaturated fatty hydrocarbon group, $R^3$ is a divalent hydrocarbon radical, optionally substituted on one or more carbon atoms with hydroxyl, more typically a straight chain or branched chain ($C_2$-$C_6$) alkylene radical, optionally substituted on one or more carbon atoms with hydroxyl, $R^4$ and $R^5$ are each independently alkyl, cycloalkyl, aryl, or aralkyl, or may be fused to form, together with the nitrogen atom to which they are each attached, form a form heterocyclic 4 to 8 membered ring, $R^6$ is absent or is H, alkyl, cycloalkyl, alkenyl, aralkyl, $O^-$, —$(CH_2)_n$—$COO^-$, or

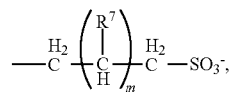

each $R^7$ is independently H or hydroxyl, n is an integer of from 1 to 4, m is an integer of from 0 to 4, more typically, of from 1 to 4, and $X^-$ is an anionic counterion, and further provided that:

if $R^6$ is absent, then the positive charge is absent from the nitrogen atom to which $R^4$ and $R^5$ are each attached and the $X^-$ counterion is absent, and if $R^6$ is $O^-$, —$(CH_2)_n$—$COO^-$, or

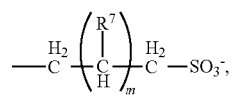

then $X^-$ counterion is absent.

In another embodiment, the surfactant composition comprises at least one surfactant compound according to structure (III):

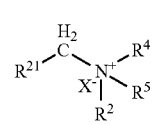 (III)

wherein:

$R^{21}$ is an is an adduct of at least one diene, typically a ($C_4$-$C_{20}$)diene, and at least one unsaturated fatty hydrocarbon group $R^4$ and $R^5$ are each independently alkyl, cycloalkyl, aryl, aralkyl, or hydrogen-terminated alkyleneoxy, or may be fused to form, together with the nitrogen atom to which they are each attached, form a form heterocyclic 4 to 8 membered ring, $R^6$ is absent or is H, alkyl, cycloalkyl, alkenyl, aralkyl, $O^-$, —$(CH_2)_n$—$COO^-$, or

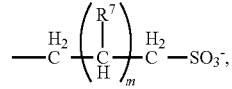

each $R^7$ is independently H or hydroxyl, n is an integer of from 1 to 4, m is an integer of from 0 to 4, more typically, of from 1 to 4, and $X^-$ is an anionic counterion, and further provided that:

if $R^6$ is absent, then the positive charge is absent from the nitrogen atom to which $R^4$ and $R^5$ are each attached and the $X^-$ counterion is absent, and if $R^6$ is $O^-$, —$(CH_2)_n$—$COO^-$, or

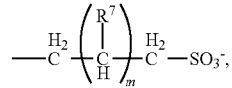

then $X^-$ counterion is absent.

In a fifth aspect, the present invention is directed to a method for handling particles, comprising dispersing the particles in an aqueous fluid comprising one or more surfactants according to the present invention to form an aqueous particle dispersion and transporting the aqueous particle dispersion by pumping the aqueous particle dispersion through a conduit.

In a sixth aspect, the present invention is directed to process for fracturing a subterranean formation, comprising pumping a fluid comprising a surfactant composition according to the present invention through a wellbore into a subterranean formation at a pressure sufficient to fracture the subterranean formation.

In a seventh aspect, the present invention is directed to a method for enhancing the recovery of oil from a reservoir having a production wellbore, comprising:

(a) introducing an aqueous flooding fluid into the reservoir at one or more locations different from the location of the production wellbore, said fluid comprising a surfactant composition according to the present invention, and
(b) recovering the oil through the production wellbore.

The diene-modified surfactant composition of the present invention provides improved thickening efficiency, improved stability of thickening performance in the presence of oil, improved stability of blends of such surfactant compounds and polymers, such as for example, polyacrylamide, reduced adsorption onto mineral surfaces, such as the surfaces of porous oil bearing rock formations, and/or improved thermal stability compared to an analogous surfactant composition derived from an unsaturated fatty acyl compound having an unsaturated fatty hydrocarbon chain that has not been modified by heating in the presence of a diene.

DETAILED DESCRIPTION OF THE INVENTION

Figure 1:
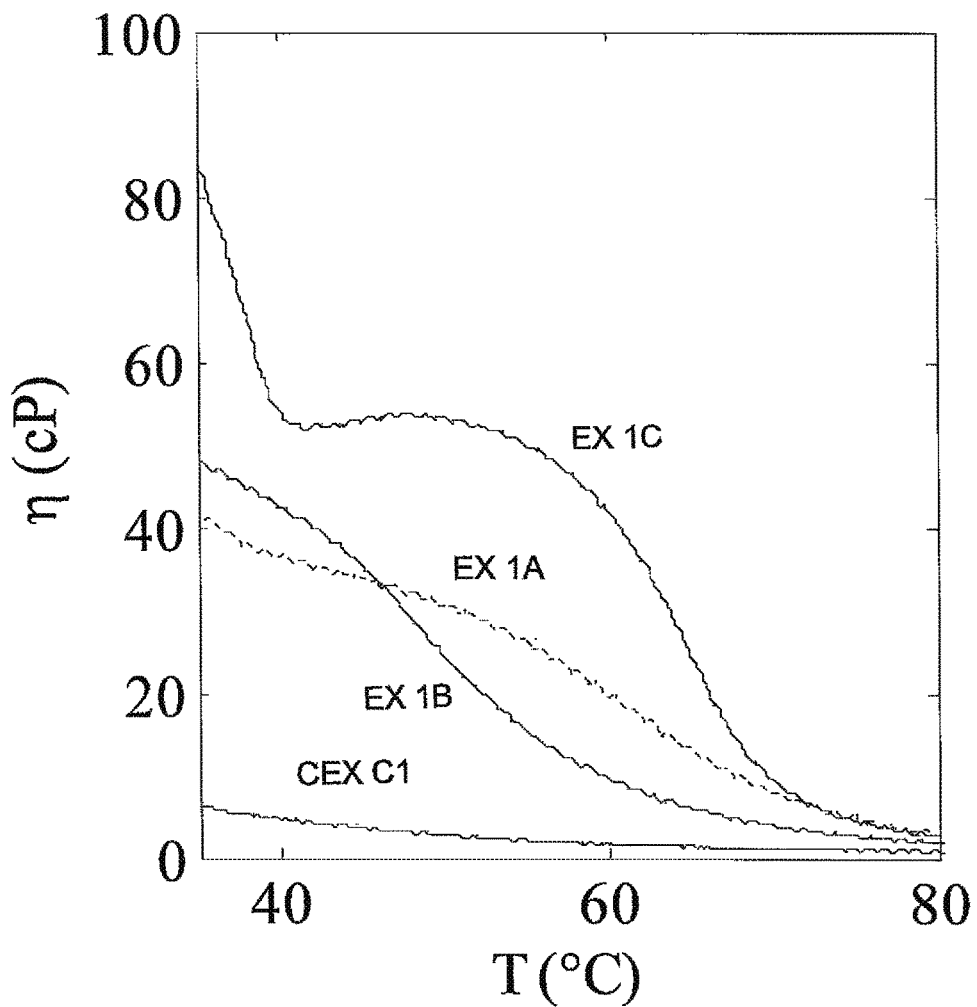
FIG. 1 shows plots of the viscosity of solutions of the respective betaine surfactant compositions of Examples 1A, 1B, and 1C, and Comparative Example 1 in brine composition 1 versus temperature.

As used herein, the terminology "($C_x$-$C_y$)" in reference to an organic group, wherein x and y are each integers, indicates that the group may contain from x carbon atoms to y carbon atoms per group.

The term "fatty", as used herein in reference to a hydrocarbon substituent, group, or chain, means that the hydrocarbon substituent, group, or chain contains from 8 to 36 carbon atoms, and, as used herein in reference to a compound, such as an acyl compound, a glyceride, or an acid, means that the compound contains at least one fatty hydrocarbon substituent, group, or chain per molecule of the compound.

As used herein, the term "adduct" means a chemical species formed by direct combination of two separate chemical moieties A and B in such a way that there is a change of connectivity, but no loss of atoms, within the moieties A and B.

As used herein, the term "acyl" means a radical according to the structure:

wherein R is a hydrocarbon group, in the case of a fatty acyl radical, R is fatty hydrocarbon group, and, in the case of an unsaturated fatty hydrocarbon radical, R is an unsaturated fatty hydrocarbon group.

As used herein, the term "alkyl" means a saturated straight chain or branched chain hydrocarbon radical, such as for example, methyl, ethyl, n-propyl, iso-propyl, n-butyl, sec-butyl, t-butyl, pentyl, n-hexyl, octyl, nonyl, decyl, undecyl, dodecyl, tridecyl, tetradecyl, pentadecyl, hexadecyl, heptadecyl, octadecyl, nonadecyl, eicosyl, uncosyl, docosyl, tricosyl, tetracosyl, and triacontyl.

As used herein, the term "alkylene" means a bivalent acyclic saturated hydrocarbon radical, including methylene, polymethylene, and alkyl substituted polymethylene radicals, such as, for example, dimethylene, tetramethylene, and 2-methyltrimethylene.

As used herein, the term "cycloalkyl" means a saturated cyclic hydrocarbon radical, such as, for example, cyclopentyl, and cyclohexyl.

As used herein, the term "alkenyl" means an unsaturated straight chain, branched chain, or cyclic hydrocarbon radical that contains one or more carbon-carbon double bonds, such as, for example, ethenyl, 2-propenyl, cis-8-heptadecenyl, cis-8-cis-11-heptadecenyl, cis-8-cis-11-cis-14-heptadecenyl, and cis-12-uncosenyl.

As used herein, the term "aryl" means a monovalent unsaturated hydrocarbon radical containing one or more six-membered carbon rings in which the unsaturation may be represented by three conjugated double bonds, which may be substituted one or more of carbons of the ring with hydroxy, alkyl, alkenyl, halo, haloalkyl, or amino, such as, for example, phenoxy, phenyl, methylphenyl, dimethylphenyl, trimethylphenyl, chlorophenyl, trichloromethylphenyl, aminophenyl, and tristyrylphenyl.

As used herein, the term "aralkyl" means an alkyl group substituted with one or more aryl groups, such as, for example, phenylmethyl, phenylethyl, and triphenylmethyl.

As used herein, "hydrogen-terminated alkyleneoxy" means a hydrogen-terminated alkyleneoxy or poly(alkyleneoxy) radical, such as, for example, a hydrogen-terminated alkyleneoxy or poly(alkyleneoxy) radical according to:

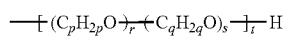

wherein:

p and q are each independently integers of from 2 to 6, more typically 2, each r is independently an integer of from 0 to about 50, each s is independently an integer of 1 to about 50, and t is an integer of from 1 to 50, provided that the product of t multiplied times the sum of r+s is less than or equal to about 50,
including, for example, hydroxyethyl, hydroxypropyl, hydroxybutyl, hydrogen-terminated poly(ethyleneoxy), hydrogen-terminated poly(propyleneoxy), hydrogen-terminated poly(butyleneoxy), and hydrogen-terminated poly (ethyleneoxy-propyleneoxy) groups, and wherein a hydrogen-terminated poly(alkyleneoxy) group contains alkyleneoxy units of two or more different compositions, for example, where both —$(C_pH_{2p}O)$— and —$(C_qH_{2q}O)$— groups, with p not equal to q, are each present, the respective alkyleneoxy units may be arranged randomly, in blocks, or in alternating order.

Suitable dienes include ($C_4$-$C_{30}$) dienes, more typically ($C_4$-$C_{30}$) conjugated dienes, that may be acyclic, such as isoprene, butadiene, and dimethylbutadiene, or cyclic, such as cyclopentadiene and cyclohexadiene.

In one embodiment, the diene comprises cyclopentadiene, one or more alkyl substituted cyclopentadienes, more typically, one or more substituted cyclopentadienes each independently substituted with a ($C_1$-$C_4$)alkyl substitutent on one or more of its ring carbon atoms or a mixture of cyclopentadiene and one or more substituted cyclopentadienes. Suitable substituted cyclopentadienes include 1-alkyl cyclopentadienes, such as, for example, 1-methyl-cyclopentadiene, 2-alkyl cyclopentadienes such as, for example, 2-methyl-cyclopentadiene, and mixtures thereof.

In one embodiment, the diene is generated in situ by charging a diene precursor, that is, compound that will form a diene under the relevant reaction conditions, to the reaction mixture for forming the addition product intermediate or the addition product of the amidoamine intermediate and diene. Suitable diene precursors include, for example, dicyclopentadiene.

Suitable unsaturated fatty acyl compounds comprise at least one unsaturated fatty hydrocarbon chain per molecule. In one embodiment, the fatty acyl compound is selected from the group consisting of unsaturated fatty glycerides, unsaturated fatty acids, and unsaturated fatty acid alkyl esters.

Suitable fatty acyl compounds include those derived from fatty triglycerides. Sources of suitable fatty triglycerides include vegetable oils, such as, for example, palm oil, soybean oil, rapeseed oil, high erucic acid rapeseed oil, sunflower seed oil, peanut oil, cottonseed oil, palm kernel oil, linseed oil, coconut oil, olive oil, safflower oil, sesame oil, crambe oil, tall oil, and canola oil, and animal fats, such as tallow, and fish oils. As used herein, "rapeseed oil" includes high erucic acid rapeseed oil as well as low erucic acid rapeseed oil, which is also called "canola oil". Variants of some of the other oils listed above are also known, such, as for example, high oleic and very high oleic sunflower and canola oils. As discussed herein, these vegetable oils may be employed in the present invention in isolated form, in altered form, such as the fatty acid and fatty acid ester forms described below, as well as a component of a triglyceride oil from a single source or mixtures of one or more of the types of oils or altered forms thereof.

A given triglyceride molecule typically comprises a glycerol moiety esterified with three fatty acid moieties. Thus, upon hydrolysis, each triglyceride molecule would yield three fatty acid residues. The distribution of specific identifiable fatty acid residues of a given oil stock is typically characterized by the amounts of the individual fatty acids as a weight percent of the total mixture of fatty acids obtained from hydrolysis of the oil stock. For example, a typical composition of the total fatty acid residue mixture derived from hydrolysis of soybean oil comprises 10.5 wt % palmitic acid, 4.5 wt % stearic acid, 23.0 wt % oleic acid, 53.0 linoleic acid, 7.5 wt % linolenic acid, and 1.5 wt % other fatty acids.

The average number of double bonds present per triglyceride molecule in an unsaturated triglyceride oil may be calculated based from the distribution of fatty acid residues of the fatty acid residue mixture produced by hydrolysis of the triglycerides of the oil. The distribution of fatty acids in a given oil may thus be readily determined by methods known to those skilled in the art. Unsaturated triglyceride oils which are particularly suitable for use in the present invention typically have an average unsaturation content of no more than about 5.0, more typically of from about 2.5 to about 3.5. For example, on average, each triglyceride molecule in soybean oil contains about 4.5 double bonds, distributed among the various hydrocarbon chains (three chains in each triglyceride molecule), i.e., soybean oil has an average unsaturation content of about 4.5. This results from the fact that soybean oil includes a mixture of triglycerides and the triglyceride molecules of soybean oil generally each have a mixture of fatty acid residues.

Another measure of characterizing the average number of double bonds present in the triglyceride molecules of an unsaturated triglyceride oil is the Iodine Value of the oil. The Iodine Value of a triglyceride or mixture of triglycerides is determined by known methods, typically, by the Wijs method (A.O.C.S. Cd 1-25). Typically, the unsaturated triglyceride oil has an Iodine Value of no more than about 150, more typically, from about 50 to about 150, even more typically, from about 70 to about 140, and, still more typically, about 80 to about 130.

In one embodiment, the unsaturated fatty acid or fatty acid alkyl ester comprises one or more compounds according to structure (II):

wherein:
$R^{11}$ is ($C_6$-$C_{30}$)alkenyl, more typically ($C_6$-$C_{24}$)alkenyl, and
$R^{12}$ is H or ($C_1$-$C_6$)alkyl.

In one embodiment, the unsaturated fatty acyl compound comprises one or more compounds according to structure (I) wherein $R^{11}$ is mono-unsaturated or poly-unsaturated ($C_6$-$C_{24}$)alkenyl, such as, for example, cis-9-hexadecenyl, all cis-7,10,13-hexadecatrienyl, cis-6-octadecenyl, trans-6-octadecenyl, cis-7-octadecenyl, cis-9-octadecenyl, trans-9-octadecenyl, cis-11-octadecenyl trans-11-octadecenyl, cis-12-octadecenyl, cis, cis-9,12-octadecedienyl, trans-9,12-octadecedienyl, all cis-6,9,12-octadecatrienyl, all cis-9,12,15-octadecatrienyl, all cis-6,9,12,15,-octadecatetraenyl, cis-11-eicosenyl, cis, cis-11,14-eicosadienyl, all cis-11,14,17-eicosatrienyl all cis-5,8,11,14-eicosatetraenyl, all cis-8,11,14,17-eicosatetraenyl, all cis-5,8,11,14,17-eicosapentaenyl, cis-13-docosenyl, cis, cis-13,16-docosadienyl, all cis-6,9,12-octadecatrienyl, all cis-7,10,13,16-docosatetraenyl, all cis-7,10,13,16,19-docosapentaenyl, all cis-4,7,10,13,16,19- docosahexaenyl, cis-15-tetracosenyl, all cis-9,12,15,18,21-tetracosapentaenyl, or all cis-6,9,12,15,18,21-tetracosahexaenyl.

Suitable unsaturated fatty acids include for example, myristoleic acid, palmitoleic acid, sapienic acid, oleic acid, elaidic acid, vaccenic acid, linoleic acid, linoelaidic acid, α-linolenic, acid, arachidonic acid, eicosapentaenoic acid, erucic acid, and docoahexanoic acid.

Suitable unsaturated fatty acids may be obtained by hydrolysis of unsaturated fatty triglycerides or of unsaturated phospholipids, or, less commonly, from hydroxycarboxylation of alkenes.

Suitable unsaturated fatty acid methyl esters may be obtained by, for example, acid-catalyzed esterification of one or more of any of the above described unsaturated fatty acids or their corresponding glycerides with a ($C_1$-$C_6$) alkanol or by transesterification of the corresponding glycerides with a ($C_1$-$C_6$)alkanol.

In one embodiment, an unsaturated fatty acyl compound is used as a starting material from which to make an unsaturated fatty tertiary amine compound, which can be accomplished by known methods, such as, for example, by:
(a) reaction of the unsaturated acyl compound to form an unsaturated fatty amide compound, such as, for example,
   (i) by aminolysis of a fatty glyceride or a fatty acid ester with ammonia, or (ii) by dehydration of a fatty acid with ammonium hydroxide,
(b) dehydration of the unsaturated fatty amide compound to form an unsaturated fatty nitrile compound,
(c) selective hydrogenation of the nitrile group of the unsaturated fatty nitrile compound to form an unsaturated fatty primary amine compound, and
(d) methylation of the unsaturated fatty primary amine compound using a formaldehyde or a formaldehyde precursor under reductive conditions to form the unsaturated fatty tertiary amine compound.

In one embodiment, the process to make the addition intermediate comprises heating the unsaturated fatty acyl compound or unsaturated fatty tertiary amine compound and the diene to an elevated temperature of up to about 300° C., more typically of from about 100° C. to about 300° C., for up to about 24 hours, more typically from about 1 hour to about 24 hours, in a closed system, such as, for example, a stainless steel agitated reactor. Typically the unsaturated fatty acyl compound or unsaturated fatty tertiary amine compound is pre-heated to reaction temperature under an inert atmosphere, for example, a nitrogen atmosphere, then the reactor is sealed and the diene component is added gradually below the surface of the liquid over a time period of about 12 hours, more typically over about 30 minutes to about 12 hours. Following further heating for a time period of up to about 24 hours, volatile components are removed by distillation, for example, the reactor may be de-pressurized while still at elevated temperature and components volatile at those conditions are removed by distillation. The extent of distillation can optionally be increased by applying vacuum to the system to reduce the pressure. The vacuum used is usually limited to retain an absolute pressure of at least 0.1 mm Hg.

The unsaturated fatty hydrocarbon chain of the at least one unsaturated fatty acyl compound or unsaturated fatty tertiary amine compound may be mono-unsaturated, that is, containing one double bond per chain, or poly-unsaturated, that is, containing two or more double bonds per chain. The two or more double bonds of a given poly-unsaturated fatty hydrocarbon chain may conjugated double bonds or non-conjugated double bonds. The non-conjugated double bonds of a polyunsaturated fatty hydrocarbon chain may, optionally, be isomerized, such as by heating and/or by the addition of a catalyst such a iodine, to form a conjugated double bonds within the unsaturated fatty hydrocarbon chain.

In one embodiment, heating the mixture of diene and unsaturated fatty acyl compound or unsaturated fatty tertiary amine compound results in formation of an adduct of the diene and the unsaturated fatty acyl compound or unsaturated fatty tertiary amine compound. A double bond of the fatty acyl compound or unsaturated fatty tertiary amine compound may act as a dieneophile, or, alternatively, one of the double bonds of the diene may act as a dienophile and reacts with a diene moiety within a fatty hydrocarbon chain of a polyunsaturated fatty acyl compound or unsaturated fatty tertiary amine compound. Also, one double bond of given diene molecule may act as a dienophile for another molecule of the diene and a given double bond of an unsaturated fatty hydrocarbon chain of the unsaturated fatty acyl compound or unsaturated fatty tertiary amine compound may act as a dieneophile for a set of conjugated double bonds on another polyunsaturated fatty hydrocarbon chain of the unsaturated fatty acyl compound or unsaturated fatty tertiary amine compound.

In one embodiment, the mixture comprising at least one diene and at least one unsaturated fatty acyl compound or unsaturated fatty tertiary amine compound is heated under conditions appropriate to form 4+2 cycloadducts, that is, Diels-Alder adducts, of the at least one diene and at least one unsaturated fatty acyl compound or unsaturated fatty tertiary amine compound.

In one embodiment, the heating the mixture of diene and unsaturated fatty acyl compound or unsaturated fatty tertiary amine compound produces an addition intermediate or addition product that comprises Diels-Alder adducts of the at least one diene and at least one unsaturated fatty acyl compound, formed by reaction of the diene with a double bond of an unsaturated fatty compound or unsaturated fatty tertiary amine compound, or by reaction of a double bond of the diene with a conjugated double bond of a polyunsaturated fatty acyl compound or unsaturated fatty tertiary amine compound. The possibility of a variety of reactions among the various unsaturated sites of the diene and the unsaturated fatty acyl compound or unsaturated fatty tertiary amine compound may produce a more diverse mixture of addition intermediates or addition products that may further include, for example, polymerized diene, such as poly(cyclopentadiene), fatty acyl compounds or unsaturated fatty tertiary amine compound with crosslinked fatty hydrocarbon chains, adducts of fatty acyl compounds or unsaturated fatty tertiary amine compound having non-crosslinked fatty hydrocarbon chains with polymerized diene, adducts of fatty acyl compounds or unsaturated fatty tertiary amine compound having crosslinked fatty hydrocarbon chains with non-polymerized diene, and adducts of fatty acyl compounds or unsaturated fatty tertiary amine compound having crosslinked fatty hydrocarbon chains with polymerized diene.

In one embodiment, a mixture of an unsaturated fatty acyl compound or unsaturated fatty tertiary amine compound and an amount of cyclopentadiene sufficient to form, on average, from 0.1 to 10 cycloadducts per molecule of the unsaturated fatty acyl compound or unsaturated fatty tertiary amine compound is heated at a temperature of at least about 200° C. for a sufficient reaction time to achieve a desired modification of the properties of the fatty acyl compound or fatty tertiary amine compound, such as, for example, an increase in thickening efficiency, and unreacted diene is removed from the mixture at the end of the reaction time (e.g., by stripping the reaction product under vacuum).

In one embodiment, the diamine comprises one or more diamines according to structure (III):

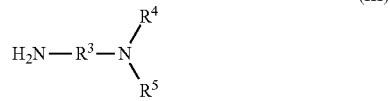

(III)

wherein $R^3$, $R^4$, and $R^5$ are each as described above.

In one embodiment, amidation of a triglyceride or other ester addition intermediate is achieved by mixing the triglyceride or other ester with from 1 to 1.5 molar equivalents, more typically from greater than 1 to 1.3 molar equivalents of diamine, typically in the presence of an acid catalyst such as formic acid, or base catalyst, such as sodium methoxide, and maintaining the mixture at an elevated temperature, typically of from greater than 100° C. to about 180° C., more typically, from about 110° C. to about 160° C., in an agitated reactor until ester groups are no longer observed by FTIR analysis. The product is then stripped of excess amine by vacuum distillation at elevated temperature of up to 180° C. and an absolute pressure of 50 mbar or less, more typically 1 mbar to 50 mbar, until no further distillate is observed.

In one embodiment, the composition of the present invention is in the form of an aqueous solution of at least one surfactant compound according to structure (I), more typically a mixture of two or more surfactant compounds according to structure (I).

In one embodiment, $R^2$ is an adduct of at least one diene selected from the group consisting of cyclopentadiene, butadiene, and isoprene, with at least one fatty hydrocarbon substituent of a vegetable oil, more typically a vegetable oil selected from the group consisting of linseed oil, canola oil, soybean oil, rapeseed oil, crambe oil, tall oil, and sunflower oil.

In one embodiment, $R^3$ is a straight chain or branched chain $(C_2-C_6)$alkylene radical, optionally substituted on one or more carbon atoms with hydroxyl.

$X^-$ may be any anion suitable to electrically balance the cation portion of the compound of structure (I), more specifically, the cation portion of the amidoamine salt or amido quaternary ammonium compound embodiments according to structure (I.b), each of which comprises a cationic nitrogen atom. Suitable anions include, for example, chloride, bromide, iodide, methosulfate, ethosulfate, p-toluenesulfonate, sulfate, phosphate, acetate, propionate, lactate, succinate, glutamate, glutarate, maleate, adipate, or polyacrylate anions. When $R^6$ is H, then $X^-$ is more typically an anionic counterion of a monovalent or polyvalent acid. When $R^5$ is alkyl, cycloalkyl, alkenyl, or aralkyl, then $X^-$ is more typically an anionic counterion of a monovalent acid.

In one embodiment, the composition of the present invention comprises at least one compound according to structure (I.a), more typically a mixture of two or more compounds according to structure (I.a):

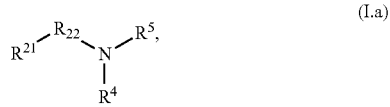

(I.a)

wherein for such one compound or independently for each of such two or more compounds, $R^{21}$, $R^{22}$, $R^4$, and $R^5$ are each as described above.

In one embodiment, the composition of the present invention comprises at least one amidoamine compound according to structure (II.a), more typically a mixture of two or more compounds according to structure (II.a):

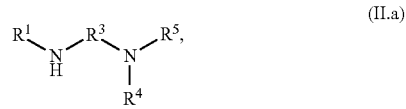

(II.a)

wherein for such one compound or independently for each of such two or more compounds, $R^1$, $R^3$, $R^4$, and $R^5$ are each as described above.

In one embodiment, the composition of the present invention comprises at least one compound according to structure (III.a), more typically a mixture of two or more compounds according to structure (III.a):

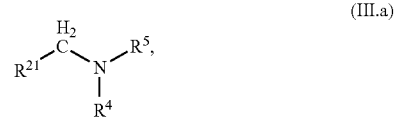

(III.a)

wherein for such one compound or independently for each of such two or more compounds, $R^{21}$, $R^4$, and $R^5$ are each as described above.

In one embodiment, the composition of the present invention comprises at least one compound according to structure (I.b), more typically a mixture of two or more compounds according to structure (I.b)

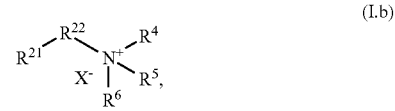

(I.b)

wherein for such one compound or independently for each of such two or more compounds:

$R^{21}$, $R^{22}$, and $X^-$ are each as described above, and $R^4$, $R^5$, and $R^6$ are each independently H, $(C_1-C_6)$alkyl, or hydrogen-terminated alkyleneoxy, more typically are each methyl.

In one embodiment, the composition of the present invention comprises at least one amidoamine salt or amido quaternary ammonium salt according to structure (II.b), more typically a mixture of two or more compounds according to structure (II.b)

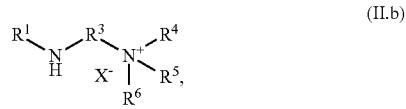

(II.b)

wherein for such one compound or independently for each of such two or more compounds:

$R^1$, $R^3$, and $X^-$ are each as described above, and $R^4$, $R^5$, and $R^6$ are each independently H or $(C_1-C_6)$alkyl, more typically are each methyl.

In one embodiment, the composition of the present invention comprises at least one compound according to structure (III.b), more typically a mixture of two or more compounds according to structure (III.b)

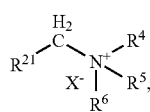
(III.b)

wherein for such one compound or independently for each of such two or more compounds:

$R^{21}$ and $X^-$ are each as described above, and $R^4$, $R^5$, and $R^6$ are each independently H, $(C_1\text{-}C_6)$alkyl, or hydrogen-terminated alkyleneoxy, more typically are each methyl.

In one embodiment of the compound according to structure (I.b), (II.b), or (III.b), $R^4$, $R^5$, and $R^6$ are each H.

In one embodiment of the compound according to structure (I.b) or (III.b), $R^4$ is $(C_1\text{-}C_6)$alkyl or hydrogen-terminated alkyleneoxy, and $R^5$ and $R^6$ are each H.

In one embodiment, the compound according to structure (II.b) is an amidoamine salt wherein $R^4$ is $(C_1\text{-}C_6)$alkyl and $R^5$ and $R^6$ are each H.

In one embodiment of the compound according to structure (I.b) or (III.b), $R^4$ and $R^5$ are each independently $(C_1\text{-}C_6)$alkyl or hydrogen-terminated alkyleneoxy, and $R^6$ is H.

In one embodiment, the compound according to structure (II.b) is an amidoamine salt wherein $R^4$ and $R^5$ are each independently $(C_1\text{-}C_6)$alkyl and $R^6$ is H.

In one embodiment of the compound according to structure (I.b) or (III.b), $R^4$, $R^5$, and $R^6$ are each independently $(C_1\text{-}C_6)$alkyl, or hydrogen-terminated alkyleneoxy.

In one embodiment, the compound according to structure (II.b) is an amido quaternary ammonium salt wherein $R^4$, $R^5$, and $R^6$ are each independently $(C_1\text{-}C_6)$alkyl.

In one embodiment, the composition of the present invention comprises at least one betaine compound according to structure (I.c), more typically a mixture of two or more compounds according to structure (I.c):

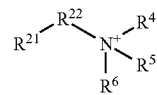
(I.c)

wherein for such one compound or independently for each of such two or more compounds:

$R^{21}$ and $R^{22}$ are each as described above, $R^4$ and $R^5$ are each independently $(C_1\text{-}C_6)$alkyl or hydrogen-terminated alkyleneoxy, $R^6$ is $-(CH_2)_n-COO^-$, and n is an integer of from 1 to 4, more typically 1.

In one embodiment, the composition of the present invention comprises at least one betaine compound according to structure (II.c), more typically a mixture of two or more compounds according to structure (II.c):

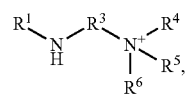
(II.c)

wherein for such one compound or independently for each of such two or more compounds:

$R^1$ and $R^3$ are each as described above, $R^4$ and $R^5$ are each independently $(C_1\text{-}C_6)$alkyl, $R^6$ is $-(CH_2)_n-COO^-$, and n is an integer of from 1 to 4, more typically 1.

In one embodiment, the composition of the present invention comprises at least one betaine compound according to structure (III.c), more typically a mixture of two or more compounds according to structure (III.c):

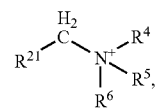
(III.c)

wherein for such one compound or independently for each of such two or more compounds:

$R^{21}$ is as described above, $R^4$ and $R^5$ are each independently $(C_1\text{-}C_6)$alkyl or hydrogen-terminated alkyleneoxy, $R^6$ is $-(CH_2)_n-COO^-$, and n is an integer of from 1 to 4, more typically 1.

In one embodiment, the composition of the present invention comprises at least one betaine according to structure (I.c) or (III.c), more typically a mixture of two or more betaine compounds according to structure (I.c) or (III.c), wherein for such one compound or independently for each of such two or more compounds:

$R^{21}$, and $R^{22}$ are each as described above, $R^4$ and $R^5$ are each independently $(C_1\text{-}C_6)$alkyl or hydrogen-terminated alkyleneoxy, $R^6$ is $-(CH_2)_n-COO^-$, and n is an integer of from 1 to 4, more typically 1.

In one embodiment, the composition of the present invention comprises at least one betaine according to structure (II.c), more typically a mixture of two or more betaine compounds according to structure (II.c), wherein for such one compound or independently for each of such two or more compounds:

$R^1$ is as described above, $R^3$ is a straight chain or branched chain $(C_2\text{-}C_6)$alkylene radical, optionally substituted on one or more carbon atoms with hydroxyl, $R^4$ and $R^5$ are each independently $(C_1\text{-}C_6)$alkyl, $R^6$ is $-(CH_2)_n-COO^-$, and n is an integer of from 1 to 4, more typically 1.

In another embodiment, the composition of the present invention comprises at least one sulfobetaine compound according to structure (I.c) or (III.c), more typically a mixture of two or more sulfobetaine compounds according to structure (I.c) or (III.c), wherein for such one compound or independently for each of such two or more compounds:

$R^{21}$ and $R^{22}$ are each as described above, $R^4$ and $R^5$ are each independently $(C_1\text{-}C_6)$alkyl or hydrogen-terminated alkyleneoxy, $R^6$ is

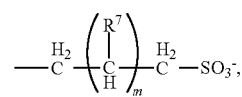

m is an integer of from 0 to 4, more typically, 1, and each $R^7$ is independently H or hydroxyl, more typically hydroxyl.

In another embodiment, the composition of the present invention comprises at least one sulfobetaine compound according to structure (II.c), more typically a mixture of two or more sulfobetaine compounds according to structure (II.c), wherein for such one compound or independently for each of such two or more compounds:
$R^1$ and $R^3$ are each as described above,
$R^4$ and $R^5$ are each independently $(C_1-C_6)$alkyl,
$R^6$ is

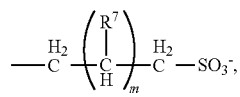

m is an integer of from 0 to 4, more typically, 1, and
each $R^7$ is independently H or hydroxyl, more typically hydroxyl.

In one embodiment, the composition of the present invention comprises at least one sulfobetaine according to structure (I.c) or (III.c), more typically a mixture of two or more sulfobetaine compounds according to structure (I.c) or (III.c), wherein for such one compound or independently for each of such two or more compounds:
$R^{21}$ and $R^{22}$ are each as described above,
$R^4$ and $R^5$ are each independently $(C_1-C_6)$alkyl or hydrogen-terminated alkyleneoxy,
$R^6$ is

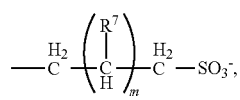

m is an integer of from 0 to 4, more typically, 1, and
each $R^7$ is independently H or hydroxyl, more typically hydroxyl.

In one embodiment, the composition of the present invention comprises at least one sulfobetaine according to structure (II.c), more typically a mixture of two or more sulfobetaine compounds according to structure (II.c), wherein for such one compound or independently for each of such two or more compounds:
$R^1$ is as described above,
$R^3$ is a straight chain or branched chain $(C_2-C_6)$alkylene radical, optionally substituted on one or more carbon atoms with hydroxyl,
$R^4$ and $R^5$ are each independently $(C_1-C_6)$alkyl,
$R^6$ is

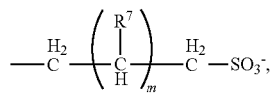

m is an integer of from 0 to 4, more typically, 1, and
each $R^7$ is independently H or hydroxyl, more typically hydroxyl.

In one embodiment, $R^6$ is $O^-$ and composition of the present invention comprises at least one amine oxide compound according to structure (I.d), more typically a mixture of two or more amine oxide compounds according to structure (I.d):

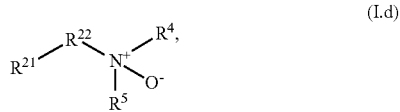

wherein, for such one compound or independently for each of such two or more compounds:
$R^{21}$ and $R^{22}$ are each as described above, and
$R^4$ and $R^5$ are each independently $(C_1-C_6)$alkyl or hydrogen-terminated alkyleneoxy.

In one embodiment, $R^6$ is $O^-$ and composition of the present invention comprises at least one amine oxide compound according to structure (II.d), more typically a mixture of two or more amine oxide compounds according to structure (II.d):

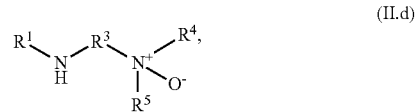

wherein, for such one compound or independently for each of such two or more compounds:
$R^1$ and $R^3$ are each as described above, and
$R^4$ and $R^5$ are each independently $(C_1-C_6)$alkyl.

In one embodiment, $R^6$ is $O^-$ and composition of the present invention comprises at least one amine oxide compound according to structure (III.d), more typically a mixture of two or more amine oxide compounds according to structure (III.d):

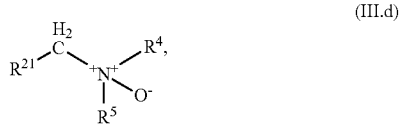

wherein, for such one compound or independently for each of such two or more compounds:
$R^{21}$ is as described above, and
$R^4$ and $R^5$ are each independently $(C_1-C_6)$alkyl or hydrogen-terminated alkyleneoxy.

In one embodiment, the composition of the present invention comprises at least on amine oxide compound according to structure (I.d) or (III.d), more typically a mixture of two or more amine oxide compounds according to structure (I.d) or (III.d), wherein for such one compound or independently for each of such two or more compounds:
$R^{21}$ and $R^{22}$ are each as described above, and
$R^4$ and $R^5$ are each independently $(C_1-C_6)$alkyl or hydrogen-terminated alkyleneoxy.

In one embodiment, the composition of the present invention comprises at least on amine oxide compound according to structure (II.d), more typically a mixture of two or more amine oxide compounds according to structure (II.d), wherein for such one compound or independently for each of such two or more compounds:
$R^1$ is as described above,
$R^3$ is a straight chain or branched chain $(C_2-C_6)$alkylene radical, optionally substituted on one or more carbon atoms with hydroxyl, and
$R^4$ and $R^5$ are each independently $(C_1-C_6)$alkyl.

In one embodiment, the composition of the present invention comprises a mixture of two or more compounds according to a structure selected from structures (I), (II), (III), (I.a), (II.a), (III.a), (I.b), (II.a), (III.b), (I.c), (II.c), (III.c), (I.d), (II.d), or (III.d) above, wherein at least one of such compounds differs from at least one of the other such compounds with respect to at least one of their respective $R^1$, $R^3$, $R^4$, $R^5$, $R^6$, and $R^{21}$ substituents.

Compounds according to the structures (I.b), (I.c), and (I.d) may each be made from the compound of structure (I.a) by known synthetic methods, such as, for example:
(i) treatment of the compound of structure (I.a) with acid to form a salt compound according to structure (I.b),
(ii) quaternization of the amine compound of structure (I.a) to form a salt according to structure (I.b),
(iii) carboxymethylation of the amine compound of structure (I.a) with, for example, sodium monchloroacetate, to form a betaine compound according to structure (I.c),
(ii) reaction of the amine compound of structure (I.a) with, for example, a sultone or with sodium 3-chloro-2-hydroxypropylsulfonate, to form a sulfobetaine compound according to structure (I.c), and
(v) oxidation of the amine compound of structure (I.a) with a hydrogen peroxide to form a compound according to structure (I.d).

Compounds according to the structures (II.b), (II.c), and (II.d) may each be made from the compound of structure (II.a) by known synthetic methods, such as, for example:
(i) treatment of the amidoamine compound of structure (II.a) with acid to form an amine salt compound according to structure (II.b),
(ii) quaternization of the amidoamine compound of structure (II.a) to form a quaternary ammonium salt according to structure (II.b),
(iii) carboxymethylation of the amidoamine compound of structure (II.a) with, for example, sodium monchloroacetate, to form a betaine compound according to structure (II.c),
(ii) reaction of the amidoamine compound of structure (II.a) with, for example, a sultone or with sodium 3-chloro-2-hydroxypropylsulfonate, to form a sulfobetaine compound according to structure (II.c), and
(v) oxidation of the amidoamine compound of structure (II.a) with a hydrogen peroxide to form an amine oxide compound according to structure (II.d).

Compounds according to the structures (III.b), (III.c), and (III.d) may each be made from the compound of structure (III.a) by known synthetic methods, such as, for example:
(i) treatment of the amine compound of structure (III.a) with acid to form an amine salt compound according to structure (III.b),
(ii) quaternization of the amine compound of structure (III.a) to form a quaternary ammonium salt according to structure (III.b),
(iii) carboxymethylation of the amine compound of structure (III.a) with, for example, sodium monchloroacetate, to form a betaine compound according to structure (III.c), and
(ii) reaction of the amine compound of structure (III.a) with, for example, a sultone or with sodium 3-chloro-2-hydroxypropylsulfonate, to form a sulfobetaine compound according to structure (III.c), and
(v) oxidation of the amine compound of structure (III.a) with a hydrogen peroxide to form an amine oxide compound according to structure (III.d).

In one embodiment, the composition of the present invention comprises one or more compounds according to structures (I.a), (II.a), (III.a), (I.b), (II.b), (III.b), (I.c), (II.c), (III.c), (I.d), (II.d), or (III.d) in the presence of minor amounts of other compounds, such as, for example, amines, diamines, fatty acids, fatty mono-, di-, and/or triglycerides, fatty methyl esters, glycerol, salts and/or side products such as oligomerized dienes, and in the case of compositions comprising compounds according to structure (I.b), (II.b), (III.b), (I.c), (II.c), (III.c), (I.d), (II.d), or (III.d), the compounds according to the respective structure (I.a), (II.a), or (III.a) from which they were derived, as well as unconverted reactants of the respective reactions (i)-(v) of the respective compounds according to structures (I.a), (II.a), and (III.a), as described above.

The addition adducts may, optionally, be reduced using various techniques, for example by hydrogenating the adduct with hydrogen in the presence of a heterogeneous noble or transition metal hydrogenation catalyst (e.g., a palladium, platinum, nickel, or highly selective copper-chromium catalyst). Methods and conditions suitable for hydrogenating the cycloaddition adducts include those typically employed to hydrogenate vegetable oil stocks, such as soybean oil.

The surfactants compounds of the present invention are useful as surfactants in a wide range of applications in areas such as personal care, such as surfactant components of personal care compositions, home care, such as surfactant components of home care compositions, oilfield services, such as surfactant components in compositions for use in formation fracturing and enhanced oil recovery processes, and agriculture, such as adjuvant components in agricultural pesticide compositions.

Underground oil reservoirs suitable for commercial production of oil initially contain sufficient energy, in the form of, for example, a gas cap, gases dissolved in the oil, or water pressure, to move oil from the reservoir into oil production wells that have been drilled into the reservoir, where the oil can then be recovered by pumping the oil from the production wellbore. After production from the reservoir has continued for some period of time, the energy available in the reservoir may be depleted to the point that it is no longer adequate to move oil to the well at a rate sufficient to allow continued profitable operation of the well. This condition may occur while large quantities of oil remain in the reservoir. Supplemental oil recovery methods, such as fracturing processes and flooding processes, have been developed to increase the rate of production from depleted oil reservoirs. In a fracturing process, an oil bearing underground formation is fractured using a highly pressurized aqueous fracturing fluid to provide additional paths for oil to flow from the reservoir to a production wellbore. In a flooding process, an aqueous flooding fluid is introduced into the reservoir to drive oil from the reservoir to a production wellbore. The flooding fluid is introduced into the oil reservoir by injecting the fluid into the reservoir at one or more injection wells at locations different from the production wellbore and the flow of fluid from the injection wells through the reservoir toward the production wellbore drives oil from the reservoir to the production wellbore.

In one embodiment, the aqueous fluid composition of the present invention is used in a method for handling of particles of debris, typically mineral particles, generated during the excavation, such as during digging, boring, drilling, blasting, dredging, or tunneling, of a geologic formation in the course of constructing a structure, such as for example, a road, bridge, building, mine, or tunnel, or drilling an oil and/or gas well. The particles generally have a particle size ranging from a fine powder to coarse gravel, e.g. dust, sand, and gravel. The debris particles are mixed with the aqueous fluid composition to form an aqueous particle dispersion and the aqueous particle dispersion is transported as needed by, for example, pumping the dispersion through a conduit. Such particle dispersions typically contain, based on 100 pbw of the liquid component of the dispersion, 90 pbw to about 99.9 pbw water, from about 0.1 pbw to about 10 pbw or, in one embodiment, from about 0.5 to about 5 pbw, of surfactant according to the present invention, and from about 5 pbw to about 150 pbw mineral particles. The particle handling method is useful in known particle handling applications, such as, for example, to transport and place mineral processing waste in underground caverns, to backfill open pits or quarries, to place clay or other liners in holding or storage, to extinguish and/or contain coal mine fires by deploying quantities of solids below ground to seal the fire from sources of oxygen, and to fill previously mined cavities with solids to prevent surface subsidence.

In one embodiment, the aqueous fluid composition of the present invention is used as the fracturing fluid in a method for hydraulic fracturing of a geologic formation to stimulate the production of fluids, such as oil and/or natural gas, from the formation. The fracturing fluid is injected through a wellbore and against a surface of the formation at a pressure and flow rate at least sufficient to initiate and/or extend one or more fractures in the formation. In one embodiment, the aqueous fluid used in the fracturing method of the present invention further comprises a proppant dispersed in the fracturing fluid. Suitable proppants are inorganic particles, such as sand, bauxite particles, or glass beads and are typically in the range of from about 20 to about 40 mesh. Such fracturing fluid compositions typically contain, based on 100 pbw of the liquid component of such composition, from about 90 pbw to about 100 pbw water, from about 0.1 pbw to about 10 pbw or, in one embodiment, from about 0.5 to about 5 pbw surfactant according to the present invention and from about 10 pbw to about 150 pbw proppant. The proppant particles are transported into fractures in the geologic formation by the pressurized fracturing fluid stream and keep the fractures from closing back down when the stream of fracturing fluid is discontinued. The proppant-filled fractures provide permeable channels through which the formation fluids can flow to the wellbore and then be withdrawn. Hydraulic fracturing fluids are subject to high temperatures and shear rates.

Typically, the flooding fluid is an aqueous brine solution having a high salt content, for example, up to about 200 grams of salt per liter of flooding fluid, more typically up to about 100 grams of salt per liter of flooding fluid, and even more typically from 5 to 80 grams salt per liter of flooding fluid. The relevant salts may be organic or inorganic salts, including monovalent, divalent, and trivalent species. Inorganic salts commonly encountered in brackish and salt water include, but are not limited to, chloride and bromide salts of potassium, sodium, calcium, magnesium, zinc, iron, and ammonium.

Injecting flooding fluid to drive oil toward the production wellbore requires the imposition of a sufficient pressure gradient to overcome the resistance of the reservoir to fluid flow. Surfactants have been added to oilfield flooding fluids to lower the surface tension at the oil/water interface in order to reduce the flooding fluid pressure and flow rate required to drive oil from the reservoir into the production wellbore.

In one embodiment, the flooding fluid comprises an amount of the surfactant composition of the present invention sufficient to lower the oil/flooding fluid interfacial surface tension of less than or equal to about 10 milliNewton per meter ("mN/m"), more typically less than or equal to about 1 mN/m, and even more typically less than or equal to about 0.1 mN/m, as determined using, for example, the drop weight method at 25° C. The amount of the surfactant composition of the present invention required to provide the desired reduction in interfacial surface tension will vary depending on a number of factors, including surfactant type, brine content in the fluid, and impurities in the flooding fluid.

Flow of the flooding fluid through the reservoir can result in undesirable short-circuiting or "fingering" of the flooding fluid through the reservoir and production of increasing amounts of water with the oil pumped form the production wellbore. Surfactants have also been used to increase the viscosity of the fluid in order to reduce fingering of the flooding fluid through the reservoir. It is desirable that the surfactant continue to provide enhanced viscosity at the elevated temperatures typically encountered under flooding conditions with an oil reservoir, which may exceed 80° C.

In one embodiment, the flooding fluid comprises an amount of the surfactant composition of the present invention sufficient to increase the viscosity of the flooding fluid greater than or equal to about 5 centiPoise ("cP"), more typically greater than or equal to about 10 cP, as measured at a shear rate of about 10 s$^-$ and a temperature of 25° C. The amount of the surfactant composition of the present invention required to provide the desired increased viscosity to the flooding fluid will vary depending on a number of factors, including surfactant type, brine content in the fluid, and impurities in the flooding fluid.

In one embodiment, the diene-modified surfactant composition of the present invention provides improved thickening efficiency, improved stability of thickening performance in the presence of oil, and/or improved thermal stability, compared to an analogous surfactant composition derived from an unsaturated fatty acyl compound having an unsaturated fatty hydrocarbon substituent that has not been modified by heating in the presence of a diene.

In one embodiment, the flooding fluid comprises an amount of the surfactant composition of the present invention sufficient to lower the oil/flooding fluid interfacial surface tension of less than or equal to about 10 mN/m, more typically less than or equal to about 1 mN/m, and even more typically less than or equal to about 0.1 mN/m, as determined using, for example, a drop weight method at 25° C., and increase the viscosity of the flooding fluid to greater than or equal to about 5 cP, more typically greater than or equal to about 10 cP, as measured at a shear rate of about 10 s$^{-1}$ and a temperature of 25° C.

In one embodiment, the flooding fluid used in the oil recovery method of the present invention comprises, on the basis of 100 parts by weight ("pbw") of the flooding fluid, from greater than 0 pbw, more typically from about 0.1 pbw, and even more typically from about 0.5 pbw to about 10 pbw, more typically to about 6 pbw of the surfactant composition of the present invention.

The amount of surfactant composition required is influenced by adsorption of surfactant compounds onto the solid mineral surfaces, for example, sandstone, limestone, or dolomite rock surfaces, of the porous oil bearing formation of the underground reservoir, that is, a larger amount of surfactant compound is required in cases of strong adsorption of the relevant surfactant compound onto the surfaces of the formation because the adsorption lowers the effective amount of surfactant compound that remains in the flooding fluid. The influence can be significant due to the very large surface area offered by a porous oil bearing rock formation of an underground reservoir.

In one embodiment, the diene-modified surfactant composition of the present invention exhibits reduced adsorption onto mineral surfaces, such as the surfaces of porous oil bearing rock formations, compared to an analogous surfactant composition derived from an unsaturated fatty acyl compound having an unsaturated fatty hydrocarbon chain that has not been modified by heating in the presence of a diene.

In one embodiment, the flooding fluid used in the oil recovery method of the present invention may further comprise other surfactants in addition to the surfactant composition of the present invention and/or other thickeners, such as polymeric thickeners, in addition to the surfactant composition of the present invention in order to further modify interfacial surface tension and viscosity characteristics of the flooding fluid.

The aqueous flooding fluid may, optionally, further comprise one or more polymers. Useful polymers include natural polymers, derivatized natural polymers, and synthetic polymers, including for example, guar gums, guar derivatives, xanthan gums, starches, starch derivatives cellulosic derivatives, polyacrylamides, and polyacrylates.

The aqueous flooding fluid may, optionally, further comprise one or more other surfactants, which may be selected from anionic surfactants, cationic surfactants, nonionic surfactants, zwitterionic surfactants, amphoteric surfactants and mixtures thereof, in addition to the diene-modified surfactants of the present invention. When present, the other surfactants are typically present in limited amounts, such as for example, from greater than 0 pbw to about 1 pbw or the other surfactants per 100 pbw of the aqueous flooding fluid.

The aqueous flooding fluid may, optionally, further comprise may optionally further comprise a gas such as air, nitrogen, or carbon dioxide to provide an energized fluid or foam. In one embodiment, the aqueous flooding fluid is in the form of a supercritical carbon dioxide emulsion.

Examples 1A, 1b, and 1C, and Comparative Example C1

The betaine surfactant composition of Example 1A was made as follows. First, a commercially available diene-modified linseed oil was reacted with 3-(dimethylamino)-1-propylamine (DMAPA) to form an amine adduct. 110 g of a diene-modified linseed oil (Dilulin™ reactive diluent, Cargill) were charged to a round-bottomed glass reaction flask equipped with vacuum, PTFE stirrer, external heat, nitrogen purge line, and water-cooled condenser that drained back to the reaction flask. While purging with nitrogen, the contents of the reaction vessel were stirred, and heated to 80° C., then 2.4 g 25% sodium methoxide in methanol was added, followed immediately by addition of 45.0 g of DMAPA. The contents of the reaction vessel were mixed for 40 minutes and the contents were heated to 130° C. and held at that temperature for 175 minutes. At that time a sample was analyzed by FTIR and found to lack an absorbance peak characteristic of carboxylic ester groups at 1740 cm$^{-1}$. The reactor was re-configured with a 10 millibar absolute vacuum source connected after a water-cooled condenser that drained to a glass flask receiver and vacuum applied while heating to a 145° C. set-point, one hour later the set-point was increased to 160° C. Thirty minutes later the reactor contents were cooled and 138 g of brown viscous liquid were collected from the reactor. The amine adduct was then reacted with sodium monochloroacetate (SMCA) to form the betaine surfactant composition. 71 g of water, 34 g of isopropanol, and 15.6 g sodium monochloroacetate were charged to a round-bottomed glass reaction flask equipped with vacuum, PTFE stirrer, external heat, nitrogen purge line, and water-cooled condenser that drained back to the reaction flask. While purging with nitrogen, the contents were stirred and 49.1 g of the amine adduct was added. Heat was applied with a 70° C. set-point. After 100 minutes of continued stirring, the temperature was increased to 80° C. and over a time period of 165 minutes portions of 50% sodium hydroxide were added sufficient to maintain the pH of the contents of the reaction vessel between 8.5 and 9.5, as measured (without correcting for temperature) on a 20% w/w dilution of samples of the reaction mixture in water. The contents of the reaction vessel were reacted a further 420 minutes with portions of 50% sodium hydroxide added to maintain the pH of the contents of the reaction vessel between 9.5 and 11.0. In total, 1.8 g of 50% sodium hydroxide was required for pH adjustment, and 12 g of samples were taken for the pH measurements. 169 g of clear yellow liquid, nominally 30% w/w active betaine, were collected at the end of the experiment.

The betaine surfactant composition of Example 1B was made by reacting, in a manner analogous to that described above in regard to Example 1A, a diene-modified linseed oil (Dilulin™ oil, Cargill Inc.) with DMAPA and then reacting, in a manner analogous to that described above in regard to Example 1A, the product of that reaction with sodium SMCA to form the betaine surfactant composition of Example 1B.

The betaine surfactant composition of Example 1C was made as follows. First, linseed oil was reacted with cyclopentadiene to form an addition intermediate. 102.8 g of linseed oil and 0.10 g phenothiazine were charged to a 300 ml capacity reaction vessel equipped with a pitch-blade agitator and baffles, external electric heat, nitrogen purge line, and sub-surface feed line from a diaphragm pump supplied by a reservoir containing a cyclopentadiene precursor (dicyclopentadiene) in a nitrogen-swept environment. While stirring at 400 revolutions per minute (rpm), the vessel was sealed and pressurized to a gage pressure of 36 pounds per square inch (psig) with nitrogen. The pressure was then relieved to atmosphere, the pressurization/vent cycle was repeated, and the after a third pressurization the pressure was relieved to 10 psig.

The contents of the reaction vessel were heated to 260° C. and the nitrogen pressurization/vent cycle was then repeated four times ending at 0 psig and the vessel was then sealed. 56.0 g of 95% dicyclopentadiene was fed into the sealed reaction vessel at a steady rate over 175 minutes while maintaining the contents of the reaction vessel at 260° C. The pressure at the end of the feed was 36 psig and fell to 24 psig after a further 120 minutes of reaction time. The contents of the reaction vessel were cooled to 120° C. at which time the residual pressure of 8 psig was vented to atmosphere and 154 g of a viscous clear liquid was collected. 118 g of the viscous clear liquid was then charged to a 250 ml round-bottomed glass reaction flask equipped with vacuum, PTFE stirrer, external heat, nitrogen purge line, and 10 millibar absolute vacuum source connected after a water-cooled condenser that drained to a glass flask receiver. While purging with nitrogen, the contents were heated to 80° C. and then the flow of nitrogen was stopped and vacuum applied. The contents of the reaction vessel were heated to 260° C. over 60 minutes and the contents were then cooled to 130° C. and the vacuum released. 105 g clear viscous liquid was recovered from the reaction flask, and 11.4 g cloudy liquid was recovered from the distillation receiver.

The amounts of reactants and yield of addition intermediate are summarized below in TABLE I below.

TABLE I

| Ingredient | Diene-modified linseed oil intermediate of EX 1C Mass (g) |
|---|---|
| Linseed oil | 102.8 |
| Phenothiazine | 0.10 |
| 95% dicyclopentadiene (5% toluene) | 56 |
| Total recovered | 154 |
| Distillation charge | 118 |
| Distillation yield | 105 |

The linseed oil/cyclopentadiene addition intermediate was then reacted, in a manner analogous to that described above in regard to Example 1A, with DMAPA to form an amine adduct and the amine adduct was then reacted, in a manner analogous to that described above in regard to Example 1A, with SMCA to form the betaine surfactant composition of Example 1C.

The betaine compound of Comparative Example C1 was made by reacting, in a manner analogous to that described above in regard to Example 1A, linseed oil with DMAPA and reacting, in a manner analogous to that described above in regard to Example 1A, the linseed oil/DMAPA reaction product with SMCA to form the betaine compound of Comparative Example C1.

The ingredients and relative amounts used in the reactions of the diene-modified linseed oil and DMAPA to form the amine adducts of Examples 1A, 1B, and 1C and the ingredients and relative amounts used in the reaction of linseed oil and DMAPA to form the amine of Comparative Example C1 are given in TABLE II below.

TABLE II

| Ingredient | Adduct of EX 1A Mass (g) | Adduct of EX 1B Mass (g) | Adduct of EX 1C Mass (g) | Adduct of CEX C1 Mass (g) |
|---|---|---|---|---|
| diene-modified linseed oil of EX 3-1 | — | — | 94.9 | — |
| Linseed oil | — | — | — | 410 |
| diene-modified linseed oil (Dilulin ™ reactive diluent) | 110.0 | 406.3 | — | — |
| DMAPA | 45.0 | 167 | 36.3 | 171.5 |
| 25% sodium methoxide in methanol | 2.5 | 9.0 | 1.5 | 9.1 |
| Total recovered after distillation | 138 | 514 | 116 | 539 |

The ingredients and relative amounts used in the reactions of the amine adducts and SMCA to form the betaine surfactant compositions of Examples 1A, 1B, and 1C and the ingredients and relative amounts used in the reactions of the amine and SMCA to form the betaine surfactant composition of Comparative Example C1 are given in TABLE III below.

TABLE III

| Ingredient | EX 1A Mass (g) | EX 1B Mass (g) | EX 1C Mass (g) | CEX C1 Mass (g) |
|---|---|---|---|---|
| Deionized water | 71.0 | 124.3 | 60.0 | 120.6 |
| Sodium monochloroacetate | 15.6 | 27.3 | 15.0 | 29.7 |
| Isopropanol | 34.0 | 60.0 | 0 | 60.0 |
| Propylene glycol | 0 | 0 | 48.0 | 0 |
| DMAPA Condensate of EX 3-2 | — | — | 50.6 | — |
| DMAPA Condensate of CEX C3-2 | — | — | — | 86.7 |
| DMAPA Condensate of EX 4-2 | 49.1 | — | — | — |
| DMAPA Condensate of EX 5-2 | — | 86.6 | — | — |
| 50% sodium hydroxide | 1.8 | 3.5 | 0 | 4.5 |
| 20% sodium hydroxide | 0 | 0 | 8.2 | 0 |
| 36% hydrochloric acid | 0.0 | 0.8 | 0.3 | 0.4 |
| Total | 171.5 | 302.5 | 182.1 | 301.9 |

The performance of the betaine compositions of Example 1B and Comparative Example C1 as viscosifying surfactants for EOR flooding fluids was compared in each of brine compositions 1 and 2, as set forth in TABLE IV below.

TABLE IV

| Salt | Brine 1 | Brine 2 |
|---|---|---|
| NaCl | 24.79 g/L | 74.37 g/L |
| KCl | 0.8 g/L | 12.4 g/L |
| $CaCl_2$, $2H_2O$ | 1.6 g/L | 4.8 g/L |
| $MgCl_2$, $6H_2O$ | 11.79 g/L | 35.37 |
| Total dissolved salts | 32 g/L | 96 g/L |

Figure 2:
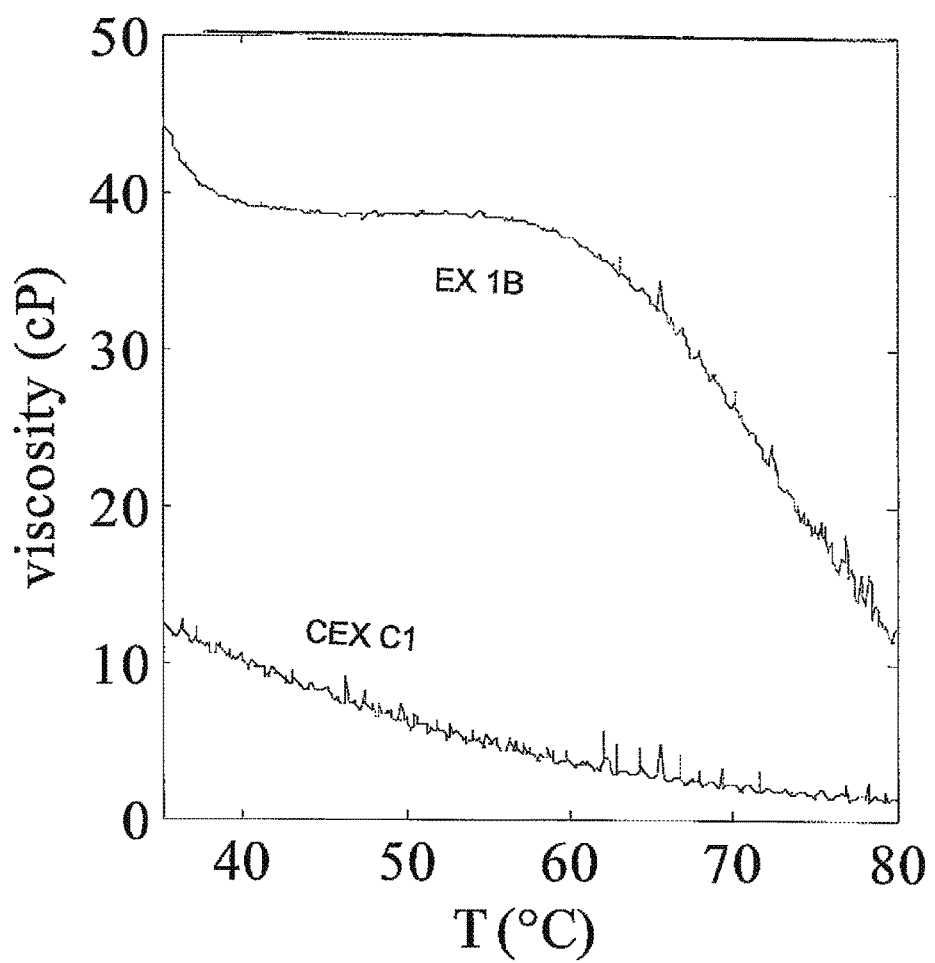
FIG. 2 shows plots of the viscosity of solutions of the respective betaine surfactant compositions of Example 1B and Comparative Example C1 in brine composition 2 versus temperature.
Figure 3:
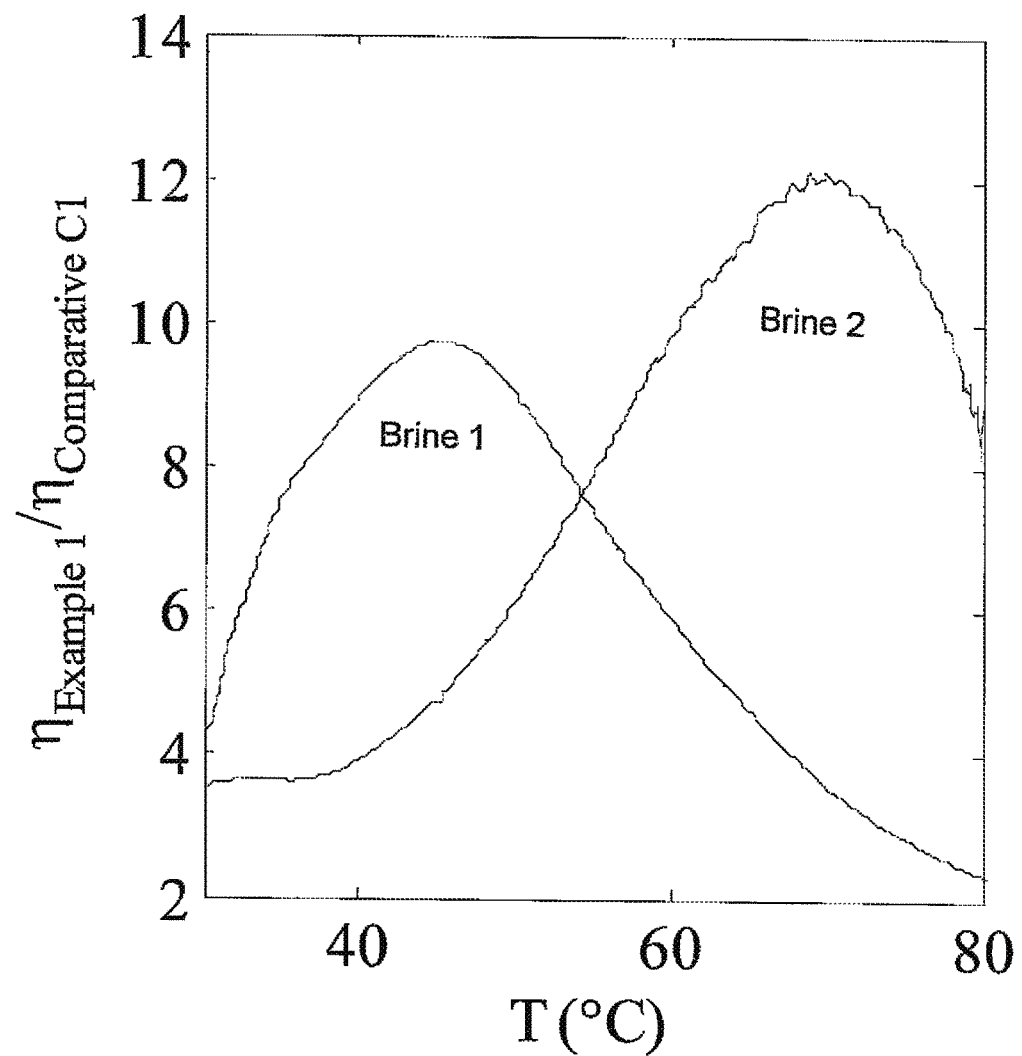
FIG. 3 shows plots of the ratios of the viscosity of a solution of the betaine surfactant of Example 1B in each of brine compositions 1 and 2 to that of analogous solutions of the betaine surfactant of Comparative Example C1 versus temperature.

The viscosity of 0.5% weight/weight solutions of the surfactants in the brines was measured between 30° C. and 80° C. at a constant shear rate of 10 $s^{-1}$ using a controlled-stress rheometer equipped with a cone—plate geometry (ARG2, TA Instruments). FIG. 1 shows a plot of the viscosity, in centiPoise (cP), of 0.5 wt % solutions of the respective betaines of Examples 1A, 1B, and 1C, and Comparative Example C1 in brine 1 versus temperature. The viscosity of the solutions of the betaine surfactant of Example 1C was higher than the viscosity of the analogous solution of betaine surfactants Examples 1A and 1B each of which was higher than the viscosity of the betaine surfactant of Comparative Example C1 and the viscosities of the various solutions begin to converge at temperatures above about 70° C. FIG. 2 shows plots of viscosity versus temperature of solution of the betaine surfactant of Example 1B and Comparative Example C1 in brine 2. FIG. 3 shows plots of the ratios of the viscosity of the solution of the betaine surfactant composition of Example 1B in each of brine compositions 1 and 2 to that of the analogous solution of the betaine surfactant composition of Comparative Example C1 versus temperature. The viscosity of the solutions of betaine surfactant of Example 1B was higher than the viscosity of the analogous solution of betaine surfactant of comparative Example C1 by a factor of from about 2 to about 12, depending on temperature and salinity.

Dynamic adsorption of the betaine compounds of Example 1B and Comparative Example C1 was measured. The test was performed at room temperature in monophasic condition using Clashach sandstone cores, in brine composition 3, as set forth in TABLE V below. Adsorption has been measured using specific miniaturized core flood test. It consists of a syringe pump that delivers constant flow rate of the surfactant solution into Clashach sandstone cores. Effluent concentration is measured thanks to a capillary viscometer positioned at the outlet of the core and adsorption is determined by measuring delay of surfactant front.

TABLE V

| Salt | Brine 3 |
|---|---|
| NaCl | 5.5 g/L |
| $CaCl_2, 2H_2O$ | 0.4 g/L |
| $MgCl_2, 6H_2O$ | 0.5 g/L |
| Total dissolved salts | 6 g/L |

Adsorption of betaine surfactant of Example 1B was found to be about 800 µg/g, which was about ⅓ the amount of adsorption, that is, 2400 µg/g, of the betaine surfactant of Comparative Example 1.

Example 2 and Comparative Example C2

The sulfobetaine compound of Example 2 was made by reacting a diene-modified linseed oil (Dilulin™ reactive diluent, Cargill Inc.) with 3-dimethylamino-1-propylamine ("DMAPA") and reacting the product of that reaction with sodium 3-chloro-2-hydroxypopyl-1-sulfonate ("NaCHPS") to form the sulfobetaine compound.

The sulfobetaine compound of Comparative Example C2 was made by reacting linseed oil with DMAPA and reacting the product of that reaction with NaCHPS to form the sulfobetaine compound.

The performance of the sulfobetaine compounds of Example 2 and Comparative Example C2 as viscosifying surfactants for EOR flooding fluids was compared in each of brine compositions 4 and 5, as set forth in TABLE VI below.

TABLE VI

| Salt | Brine 4 | Brine 5 |
|---|---|---|
| NaCl | 74.37 g/L | 148.74 gL |
| KCl | 2.4 g/L | 4.8 g/L |
| $CaCl_2, 2H_2O$ | 4.8 g/L | 9.6 g/L |
| $MgCl_2, 6H_2O$ | 35.37 | 70.74 g/L |
| Total dissolved salts | 96 g/L | 192 g/L |

Figure 4:
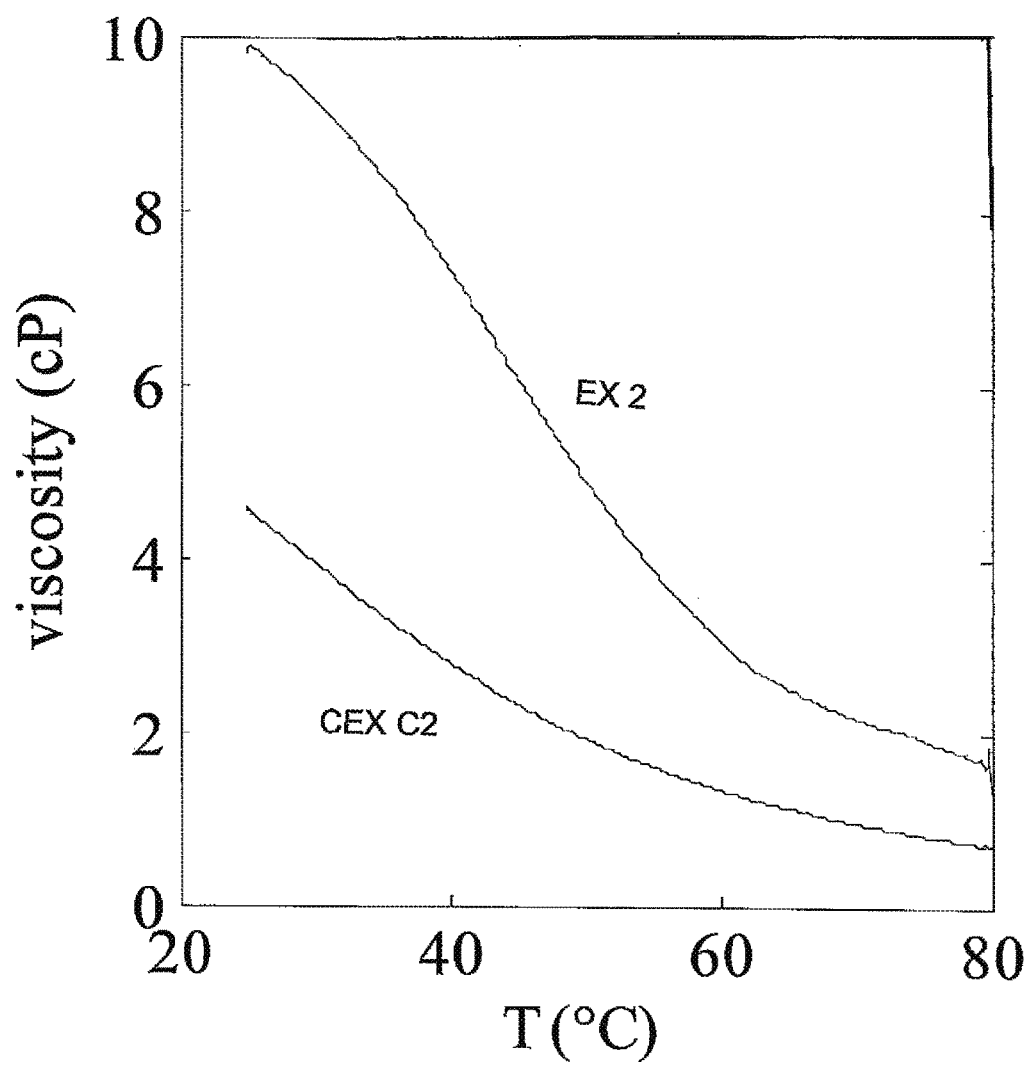
FIG. 4 shows plots of the viscosity of solutions of the respective sulfobetaine surfactant compositions of Example 2 and Comparative Example C2 in brine composition 4 versus temperature.
Figure 5:
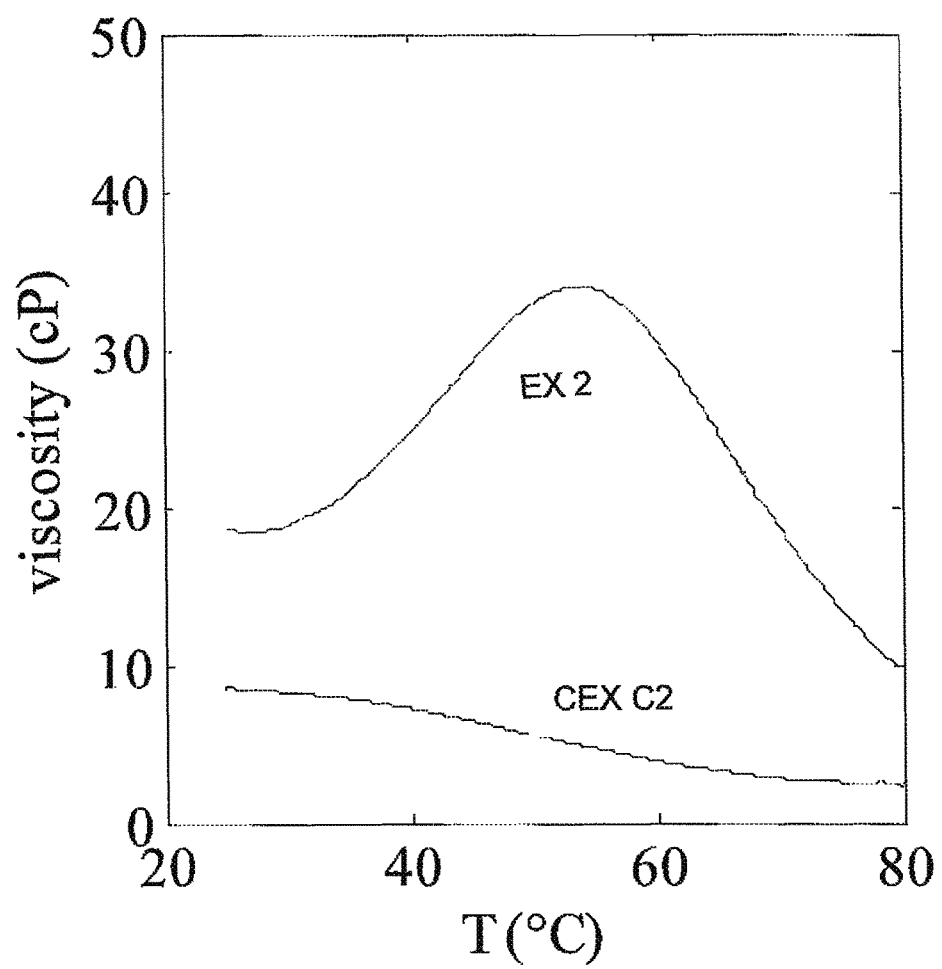
FIG. 5 shows plots of the viscosity of solutions of the respective sulfobetaine surfactant compositions of Example 2 and Comparative Example C2 in brine composition 5 versus temperature.
Figure 6:
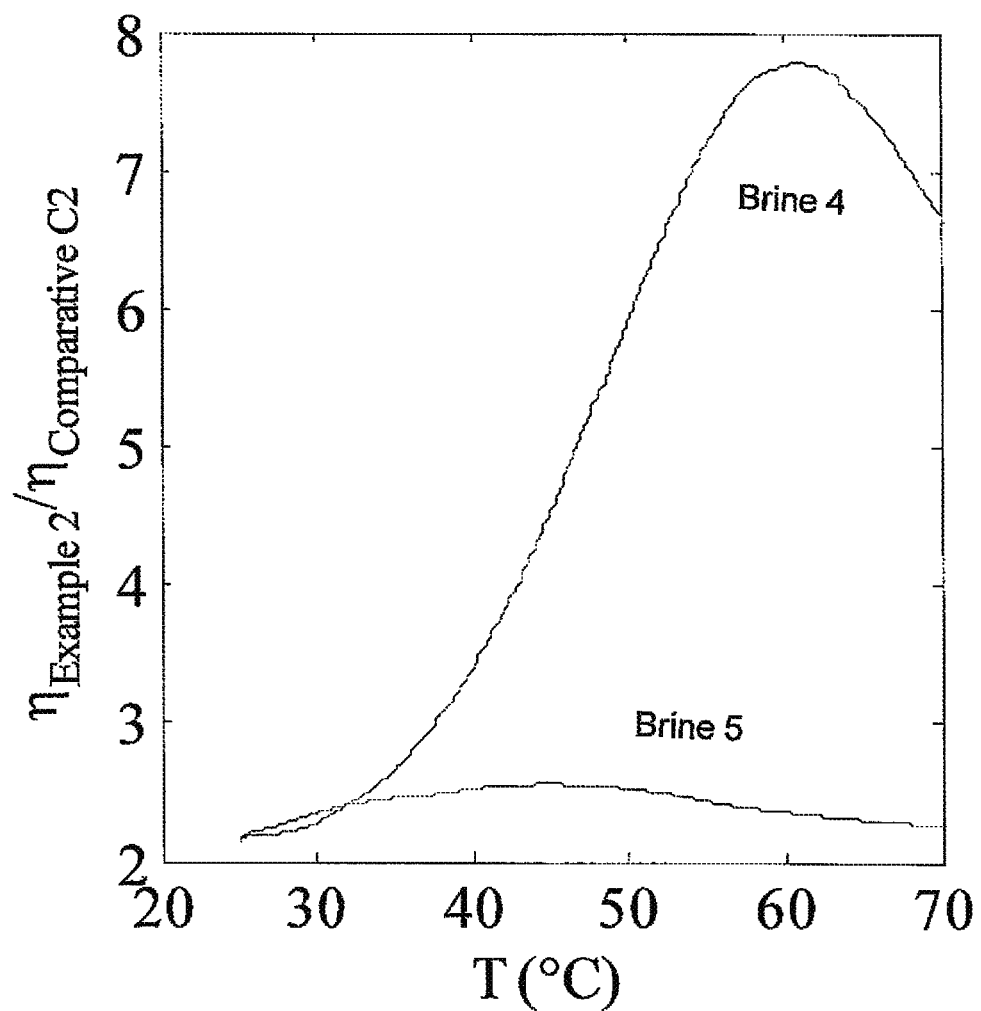
FIG. 6 shows plots of the ratios of the viscosity of a solution of the sulfobetaine surfactant of Example 2 in each of brine compositions 4 and 5 to that of analogous solutions of the sulfobetaine surfactant of Comparative Example C2 versus temperature.

The viscosity of 0.5% weight/weight solutions was measured between 25° C. and 80° C. at a constant shear rate of 10 $s^{-1}$ using a controlled-stress rheometer equipped with a cone—plate geometry (ARG2, TA Instruments). FIG. 4 shows plots of viscosity versus temperature of solution of the sulfobetaine surfactant of example 2 and Comparative Example C2 prepared in brine 4. FIG. 5 shows plots of viscosity versus temperature of solutions of the betaine surfactant of Example 2 and Comparative Example C2 prepared in brine 5. FIG. 6 shows plots of the ratios of the viscosity of the solution of the sulfobetaine surfactant of Example 2 in each of brine compositions 3 and 4 to that of the analogous solution of the sulfobetaine surfactant of Comparative Example C2 versus temperature. The viscosity of the solutions of sulfobetaine surfactant of Example 2 was higher than the viscosity of the analogous solution of sulfobetaine surfactant of Comparative Example C2 by a factor of from about 2 to about 8, depending on temperature and salinity.

The invention claimed is:

1. A dimethyl amine adduct, comprising the product obtained by:
   (1)(a) forming an addition intermediate by heating a mixture comprising at least one diene and at least one unsaturated fatty acyl compound, and
   (b) reacting the addition intermediate with a 3-(dimethylamino)-1-propylamine to form the dimethyl amine adduct, or
   (2)(a) reacting at least one unsaturated fatty acyl compound with at least one 3-(dimethylamino)-1-propylamine to form an amidoamine intermediate, and
   (b) heating a mixture of the amidoamine intermediate and at least one diene to form the dimethyl amine adduct;
   wherein the diene is a ($C_4$-$C_{30}$) conjugated diene selected from the group consisting of isoprene, butadiene, dimethylbutadiene, and dicyclopentadiene.

2. A surfactant composition comprising at least one diene-modified dimethyl surfactant compound comprising a cycloadduct and derived from a dimethyl amine adduct according to claim 1, wherein the at least one diene-modified dimethyl surfactant compound is derived from the amine adduct by:
   (a) treatment of the adduct with acid to form an amine salt surfactant compound,
   (b) quaternization of the adduct to form a quaternary ammonium salt surfactant compound,
   (c) carboxymethylation of the adduct to form a betaine surfactant compound,
   (d) reaction of the adduct with a sultone or a sulfonate, to sulfobetaine surfactant compound, or
   (e) oxidation of the adduct to form an amine oxide surfactant compound.

3. A method for handling particles, comprising dispersing the particles in an aqueous fluid comprising one or more surfactants according to claim 2 to form an aqueous particle dispersion and transporting the aqueous particle dispersion by pumping the aqueous particle dispersion through a conduit.

4. A process for fracturing a subterranean formation, comprising pumping an fluid comprising a surfactant composition according to claim 2 through a wellbore into a subterranean formation at a pressure sufficient to fracture the subterranean formation.

5. A method for enhancing the recovery of oil from a reservoir having a production wellbore, comprising:
   (a) introducing an aqueous flooding fluid into the reservoir at one or more locations different from the location of the production wellbore, said fluid comprising a surfactant composition according to claim 2, and
   (b) recovering the oil through the production wellbore.

* * * * *